United States Patent [19]

Butler

[11] Patent Number: 5,091,621
[45] Date of Patent: Feb. 25, 1992

[54] METHOD AND APPARATUS FOR DESTROYING A SYRINGE NEEDLE

[76] Inventor: William F. Butler, 680 Atlanta Country Club Dr., Marietta, Ga. 30067

[21] Appl. No.: 532,021

[22] Filed: Jun. 1, 1990

[51] Int. Cl.$^5$ ............................ B23H 9/00; H05B 3/00
[52] U.S. Cl. ........................................ 219/68; 83/944
[58] Field of Search ................. 219/68; 128/919; 241/37.5, 65; 83/944; 200/11 C, 61.64

[56] References Cited

U.S. PATENT DOCUMENTS

| | | | |
|---|---|---|---|
| 3,770,930 | 11/1973 | Tang | 200/61.64 |
| 4,628,169 | 12/1986 | Ch'ing-Lung | 219/68 |
| 4,877,934 | 10/1989 | Spinello | 219/68 |
| 4,890,006 | 12/1989 | Huang | 200/11 C |
| 4,961,541 | 10/1990 | Hashimoto | 219/68 |
| 4,965,426 | 10/1990 | Colombo | 219/68 |

Primary Examiner—Geoffrey S. Evans
Attorney, Agent, or Firm—Jones, Askew & Lunsford

[57] ABSTRACT

A method and apparatus for destroying a syringe needle, having a housing, first and second walls in opposed relationship in the housing and defining therebetween a needle burn chamber, the distance between the first and second surfaces being at least the length of the needle, the first surface defining a first opening therethrough, a needle receiving enclosure in the chamber movable between the first and second surfaces and defining a second opening therethrough which is coaxial with the first opening, a first electrical contact on the needle receiving enclosure, a second electrical contact on the second surface and being in registry with the second opening, power source connected to the first and second contacts, a waste collector disposed in the housing beneath and in communication with the burn chamber, the waste collector being removable from the housing and a mechanism that moves the needle receiving enclosure toward the first opening; so that when the needle is inserted through the first and second openings to be in contacting relationship to the needle receiving enclosure and the needle receiving means is moved toward the second surface, the tip of the needle engages the second contact closing the circuit between the contacts and melting the needle along at least most of its length with the resultant melted waste falling into the waste collector.

6 Claims, 2 Drawing Sheets

METHOD AND APPARATUS FOR DESTROYING A SYRINGE NEEDLE

BACKGROUND OF THE INVENTION

This invention relates to a method and apparatus for destroying the steel portion of a syringe.

The threat of infectious diseases and, of course, in particular AIDS and hepatitis B, is very prevalent today in hospitals and doctors' offices as a result of the use of hypodermic syringes. The Center for Disease Control in Atlanta has extensively studied accidental syringe sticking incidents and have logged where most of the accidents occur and to whom. The Center's records indicate that nurses experience more incidents than most other medical personnel.

Re-covering the needle with the plastic tip cover provided with the syringe after use has not solved the problem since the cover can come off or the person can be stuck by merely attempting to place the cover on the needle. Other means presently utilized for the disposal of used syringes still leave the steel of the hypodermic needle on the syringe, thereby exposing the waste handlers to the possibility of being pricked. The present syringe disposal systems are also very expensive.

The prior art includes U.S. Pat. No. 4,628,169 which discloses an apparatus for melting only the tip of the needle, with the remainder of the metal on the syringe, which still may be contaminated, being detached by a separate operation. That system still leaves the possibility of the person collecting the remaining needle portion being exposed to a disease thereon. Also, any infectious fluids are still available to flow out of the now-open plastic portion of the syringe.

SUMMARY OF THE INVENTION

The above disadvantages of the prior art are overcome by the present invention which comprises a device that electrically destroys the entire steel portion of the hypodermic syringe. While applying a safe, low voltage to the steel portion of the needle, the steel melts below the plastic portion of the syringe, welding closed the hollow portion of the needle to prevent any fluid in the syringe to flow from it. The now-sterilized metal melt down is collected for easy removal and can be discarded in a ordinary trash container.

The device comprises a housing having a battery power source, such as a 12-volt battery, and associated circuitry. A needle burning chamber is provided in the housing that has a stationary first electrical contact that is mounted on one wall of the chamber. The second contact is mounted on a needle receiving means that is movable within the chamber from a first position adjacent an opening in another wall of the chamber to a second position adjacent the other wall and the first contact. The needle receiving means is normally spring-biased in the first position. A waste receiving means is located beneath the burning chamber. The battery can be readily or continuously re-charged.

The needle receiving means comprises a metal ring to which the second contact is connected. An opening is provided in the center of the ring that is in registry with the opening in the burning chamber wall.

In operation, the power source is energized and the metal needle portion is inserted into the needle receiving means which is then pushed toward the back wall of the burning chamber and the first electrical contact. When the tip of the needle engages that contact, the needle completes the circuit and acts as a jumper between the two electrical contacts. The current then begins to melt the needle along its length as the needle receiving means is continually pushed towards the first contact. The melted metal drops into the waste receiving means to be collected at a later time.

The plastic portion of the needle is then withdrawn from the needle receiving means. It can be retrieved for recycling.

It is, therefore, an object of the present invention to provide a safe, low cost, efficient and easy to use device for the destruction of the metal portion of a hypodermic syringe, thereby killing any infectious virus thereon or therein.

Another object of this invention is to completely remove the metal needle from a syringe while simultaneously sealing the plastic portion of the syringe.

These and other advantages will be apparent from the following description of the invention.

BRIEF DESCRIPTION OF THE FIGURES OF DRAWINGS

DETAILED DESCRIPTION OF THE PREFERRED EMBODIMENT

Figure 1:
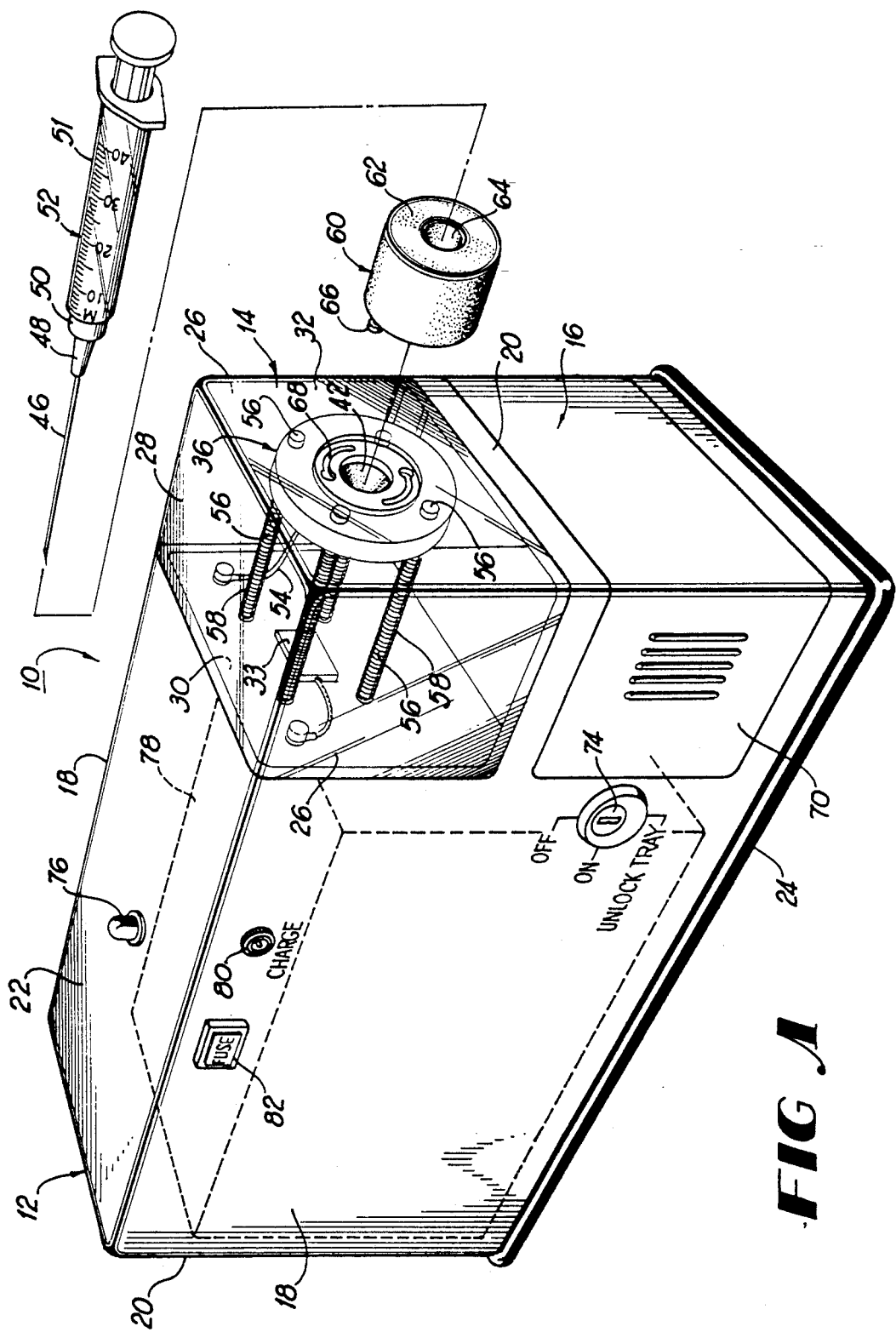
FIG. 1 is perspective view of the present invention with the needle guide means and a syringe in exploded view away for clarity.

The numeral 10 denotes generally the present invention which comprises a housing 12, a burning chamber 14 and waste collection means 16. The housing 12 can be made of any suitable material, such as metal, and is generally rectangular in shape with side walls 18, end walls 20 and top 22. A support flange 24 extends about the bottom periphery of the housing 12 to provide stability for the device when it is placed on a suitable support surface.

The burning chamber 14 occupies the upper quadrant of one end of the housing 12 and preferably is constructed of a heat resistant material. The chamber 14 is defined by side walls 26, a top 28, rear wall 30 and front wall 32. A first electrical contact 33 is mounted on rear wall 30 in registry with an opening 34 centrally disposed through front wall 32.

Figure 2:
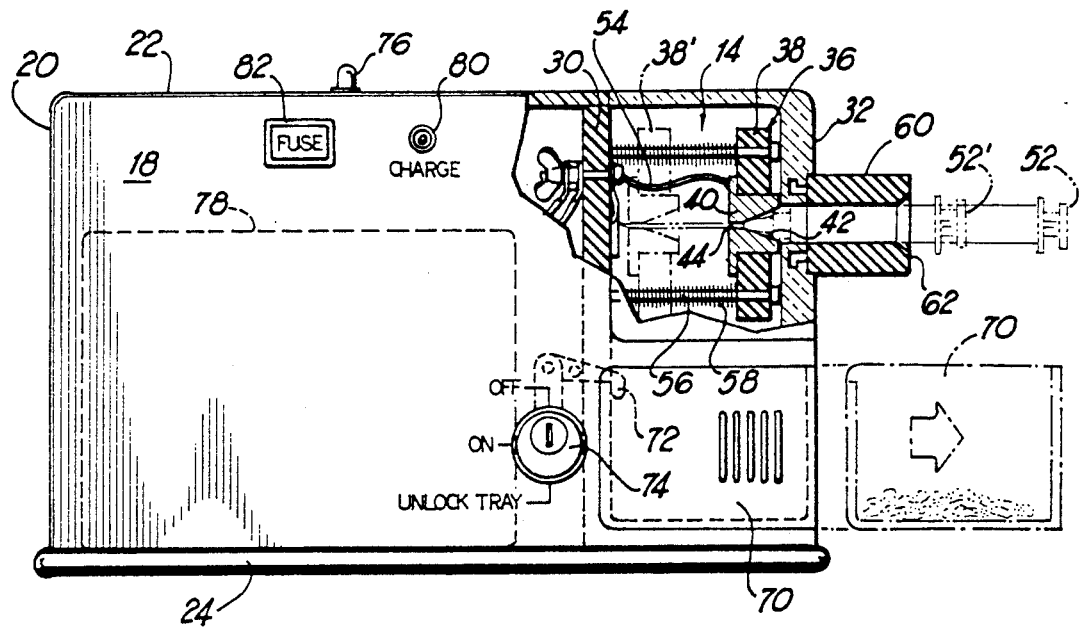
FIG. 2 is a side elevational view in partial cross-section of the invention.
Figure 3:
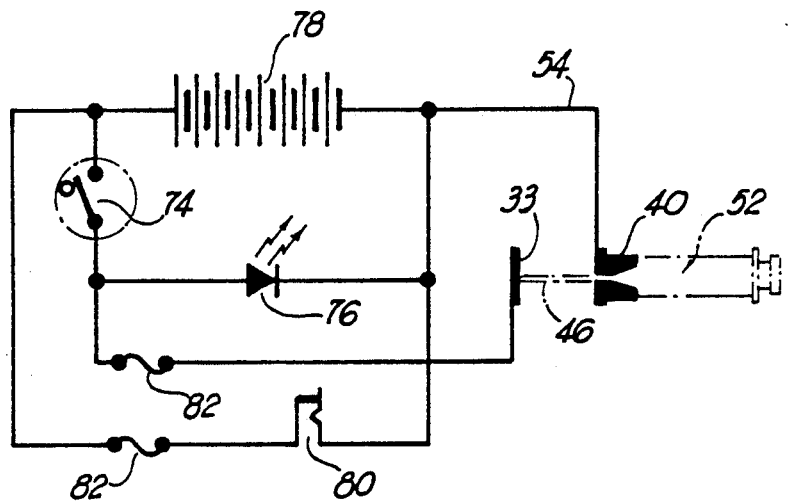
FIG. 3 is a schematic of the electrical circuitry of the present invention.

As seen more clearly in FIG. 2, a needle receiving means 36 is provided within the chamber 14 and comprises a circular, non-conductive plate 38 having as electrically conductive plug 40 positioned through its center. A conical shaped port 42 is disposed through the front face of the plug 40 adjacent wall 32 and which tapers downwardly through the interior of the plug 40 to terminate in opening 44 which exits the rear face of plug 40. The port 42 and opening 44 are dimensional to receive the metal needle portion 46, the neck portion 48 and shoulder portion 50 on body portion 51 of the hypodermic needle 52. Wire 54 connects the plug 40 with the electrical circuitry within housing 12 through rear wall 30.

The plate 38 is mounted within the chamber 14 for movement between a rest position adjacent opening 34 and an operative position as shown in phantom lines in FIG. 2 at 38' adjacent the rear wall 30 along a plurality of posts 56 that extend outwardly from wall 30. The plate 38 is normally biased in its rest position by springs 58.

Needle guide means 60 is provided on the wall 32 exteriorly of the chamber 14 and comprises a circular element 62 having a central bore 64 therethrough. The element 62 is detachably mounted to the wall 32 by means of bayonet lugs 66 which are engageable within complementary slots 68 on wall 32. The size of bore 64 depends on the diameter of the needle body 51 utilized. Thus, a different sized needle 52 would require its own respective guide means 60 to be placed on the wall 32.

The diameter of opening 44 can be of such size as to accept conventional 22-, 18-, 14- or any other gauge stainless steel needles therethrough. Additionally, the device 10 may incorporate a plurality of needle receiving means so that a single device 10 may be used to destroy a number of different style and diameter needles, such as for examples intravenous and. catheter placement needles.

The waste collection means 16 is disposed beneath and in communication with the burn chamber 14 and comprises a tray 70 that is slidably removable from housing 12, as shown in FIG. 2. The tray 70 receives therein the melted needles that result from the operation of the device 10.

The tray 70 is detained within the housing 12 by means of a locking arm 72 that is operatively connected to the keylock switch 74. The switch 74 is a safety feature, ensuring that only authorized personnel operate the device 10. The "unlock tray" position of the switch 74 releases the locking ar 72 and allows the tray 70 to be removed.

A LED light 76 is positioned on top 22 that is on when the switch 74 is moved to the "ON" position. The power source is normally a 12-volt battery 78 that is rechargeable through charging opening 80 in side wall 18. The fuses 82 within the housing 12 are reached through fuse opening 82. A second LED light, not shown, may be provided to indicate that the charging circuit is in use.

OPERATION

To operate the device 10, a key is inserted into switch 74 which is turned to the "ON" position, which in turn allows electricity to flow from battery 78 to contact 33 and to plug 40. The light 76 will also be illuminated, indicating that the device 10 is operative.

The user inserts the needle 52 into bore 64 until the shoulder 50 engages the port 42. The needle portion 46 then receives current along its length through plug 40. The position of the needle 52 at that time is shown in FIG. 2 at numeral 52'. The distance between the contact 33 and plug 40 is at least equal to the length of the needle portion 46 desired to be melted.

The user begins to push the needle 52 through the element 62, thereby moving plate 38 towards wall 30 until the tip of the needle portion 46 engages contact 33. The needle portion 46 then acts as a jumper between contact 33 and plug 40, closing the circuit and melting the needle portion 46. Continued pushing of the needle 52 causes the plate 38 to assume its position 38', at which time, the majority of the metal needle portion 46 has melted off of the needle 52 and has fallen into the tray 20.

The user then withdraws the needle 52 from the device 10, allowing the plate 38 to assume its rest position. At that time, another needle 52 may be inserted into the device 10 or the device 10 can be de-energized by turning the switch 74 to the "OFF" position. The light 76 will then go off, indicating that the device 10 is inoperative.

When enough waste has been collected in tray 70, it can be removed by turning the switch 74 to the "UNLOCK TRAY" position. The contents of the tray 70 are sterile, so they can be disposed of as normal waste materials. The tray 70 will contain no sharp metal so incidents of sticking will be minimalized or eliminated. The remaining body portion 51 of the needle 52 can be recycled as sterilized plastic.

What is claimed is:

1. An apparatus for destroying a syringe needle, comprising:
   (a) a housing;
   (b) first and second substantially vertically oriented surfaces in opposed relationship in the housing, and defining therebetween a needle burn chamber, the distance between the first and second surfaces being at least the length of the syringe needle, the first surface defining a first opening therethrough;
   (c) a substantially horizontal needle receiving means with guide means comprising posts between the surfaces and a biasing means comprising springs on the posts in the chamber movable between the first and second surfaces and defining a second opening therethrough which is coaxial with the first opening;
   (d) a first electrical contact on the needle receiving means;
   (e) a second electrical contact on the second surface and being in registry with the second opening;
   (f) power means connected to the first and second contacts; and
   (g) means for normally biasing the needle receiving means toward the first opening so that when the needle is inserted in a substantially horizontal manner through the first and second openings to be in contacting relationship to the needle receiving means and the needle receiving means is moved toward the second surface, the tip of the needle engages the second contact closing the circuit between the contacts and melting the needle along at least most of its length.

2. An apparatus as claimed in claim 1 further comprising a waste collecting means disposed in the housing beneath and in communication with the burn chamber.

3. An apparatus as claimed in claim 1 wherein the needle receiving means is a circular plate.

4. An apparatus as claimed in claim 1 and further comprising a needle guide means detachably mounted on said needle receiving means exteriorly of said housing, said guide means having a channel therethrough of a specific diameter corresponding to the diameter of said needle.

5. An apparatus as claimed in claim 2, wherein said waste collecting means is removable from said housing and lock means are provided on said waste collecting means.

6. A method of destroying a syringe needle, having a metal portion, comprising the steps of:
   (a) inserting the metal portion of a needle through a substantially horizontal needle receiving means with guide means comprising posts and a biasing means comprising springs on the posts into a needle burn chamber having a first electrical contact on the needle receiving means and a second electrical contact on a wall of the chamber opposite the needle receiving means;
(b) energizing the contacts;
(c) moving the needle receiving means toward said wall until the metal portion engages the second electrical contact, closing the circuit between the contacts; and
(d) pushing the needle receiving means toward the wall until at least a major portion of the metal portion is melted along its length.

* * * * *